United States Patent [19]

McDonald

[11] Patent Number: 6,030,578
[45] Date of Patent: Feb. 29, 2000

[54] COUPLING ASSEMBLY FOR THE STERILE TRANSFER OF STERILE MATERIALS BETWEEN A TRANSPORTABLE CONTAINER AND A STERILE ENCLOSURE

[75] Inventor: Austin McDonald, Raritan, N.J.

[73] Assignee: Duras Trading Limited, Dublin, Ireland

[21] Appl. No.: 08/860,911

[22] PCT Filed: Jan. 15, 1996

[86] PCT No.: PCT/IE96/00001

§ 371 Date: Sep. 15, 1997

§ 102(e) Date: Sep. 15, 1997

[87] PCT Pub. No.: WO96/21615

PCT Pub. Date: Jul. 18, 1996

[30] Foreign Application Priority Data

Jan. 13, 1995 [IE] Ireland .................................. S950020

[51] Int. Cl.[7] .................. A61L 2/10; A61L 2/02
[52] U.S. Cl. .................. 422/24; 422/22; 422/186; 422/186.3; 250/492.1; 250/496.1; 250/428
[58] Field of Search .................. 422/22, 24, 186, 422/186.3; 250/492.1, 496.1, 428

[56] References Cited

U.S. PATENT DOCUMENTS

| | | | |
|---|---|---|---|
| 5,130,093 | 7/1992 | Wieczorek | 422/26 |
| 5,446,289 | 8/1995 | Shodeen et al. | 250/455.11 |
| 5,447,699 | 9/1995 | Papciak et al. | 422/294 |

Primary Examiner—Elizabeth McKane
Assistant Examiner—Fariborz Moazzam
Attorney, Agent, or Firm—Thomas L. Bohan

[57] ABSTRACT

A coupling assembly for the sterile transfer of sterile materials between a transportable container and a sterile enclosure includes a closeable dock of the enclosure which seals with a closeable mouth of the container to define between them a sealed connecting chamber. A UV light source mounted within the chamber is activated to generate UV light to sterilize the interior of the chamber. Closures of the container mouth and dock are then displaced to provide a communication path between the interiors of the container and enclosure.

20 Claims, 13 Drawing Sheets

COUPLING ASSEMBLY FOR THE STERILE TRANSFER OF STERILE MATERIALS BETWEEN A TRANSPORTABLE CONTAINER AND A STERILE ENCLOSURE

The present invention relates to apparatus for use in isolation and/or containment processes. More particularly, the invention relates to apparatus for assisting in component transfer during aseptic manufacturing processes which may be undertaken in a traditional clean room or in an isolation and/or containment system employed for operator and/or process protection.

Sterility maintenance is of vital concern in many manufacturing processes, to safeguard against contamination of products being manufactured in the process. Exemplary industries using aseptic production in a traditional manner or in isolation and/or containment facilities include the bulk and finished pharmaceuticals, medical devices, biotechnology, radiopharmaceutical and food industries.

In such facilities, a particular difficulty arises where components for use in manufacture are required to be transferred from one sterile process enclosure to another. In clean room applications, where components are introduced to the processing enclosure via an autoclave, extreme care is necessary to ensure that the potential for recontamination of the component containers is minimised. Traditionally, where isolation and/or containment is used, such transfers resulted in significant down-times during which isolation and/or containment facilities were breached to enable components to be entered and/or removed after which the integrity of the isolated and/or contained area had to be re-established to ensure the integrity of the processing environment. More recently, developments in isolation and/or containment facilities led to the introduction of specialised mating ports which can be deployed to enable components to be transferred from one area to the other without breach of isolation and/or containment. While representing a significant advance in isolation and/or containment technology, these ports are not without disadvantage. Commonly, the required location in the process enclosure is provided with a port which engages sealingly with a corresponding port of a transfer container, finite seals being used to mask gross potential contamination. The mated ports can then be opened to enable materials or components to be transferred from one area to another. One particular problem associated with the use of such transfer ports relates to their use in aseptic transfers. The presence of the seal or seals (normally made of silicon) is in itself a disadvantage in that it represents an area via which potential contamination which can be present on the exposed perimeter of the finite seals can be transferred into the sterile process enclosure of the isolation and/or containment facility. Additionally, suitable disposable ports used for component transfers are normally manufactured from plastics materials which do not withstand the high temperatures reached during autoclaving. Where these transfer ports need be used under aseptic conditions, their inability to withstand high temperature sterilisation, for example using steam, constitutes a significant disadvantage.

Under optimised conditions, the known transfer port described above is only capable of providing sterility assurance levels of $10^{-3}$ on the basis of finished product. While acceptable for many purposes, even greater levels of sterility assurance are desirable or required in some industries. For example, in the pharmaceuticals field, sterility assurance levels of $10^{-6}$ are desirable. That is to say, a reduction by a factor of a million or $10^{-6}$ of the viable contaminants is desirable. Other disadvantages relate to the composition of the ports in that they are complex toleranced elements which contain many parts bonded together with seals and so are relatively expensive to produce. Yet a further disadvantage is that manufacturing tolerances limit the effective physical size of the disposable plastic ports to 100 mm diameter or less.

It is an object of the present invention to provide apparatus and a method for the transfer of materials between process enclosures in a manner in which greater sterility assurance levels can be achieved than were heretofore available. It is also an object to provide such apparatus which is of a high quality manufacture, more cheaply and in a more versatile form than previously available.

The invention therefore provides apparatus and a process in accordance with the claims.

The present invention accordingly provides a coupling assembly for use in the sterile transfer of sterile materials between a transportable container and a sterile enclosure, the assembly comprising sterilising means, a first coupling member on the container engageable with a second coupling member on the enclosure and engaging means associated with each of the coupling members for sealingly interengaging the container and the enclosure, the first coupling member including a removable container closure and the second coupling member including a removable closure for the enclosure so that on interengagement the closures define between them a sealed connecting chamber, the sterilising means being contained substantially within the sealed connecting chamber and being operable to generate in the chamber a sterilising medium for sterilising the chamber and its internal surfaces.

The sterilising means may be means for generating any of the following sterilising media, namely radiation such as gamma, electron beam, ultraviolet radiation (UV) or pulsed light. The term "pulsed light" as used herein refers to light produced by storing electrical energy in a high energy density electrical storage capacitor and releasing it in short, high intensity pulses, generating high peak power levels. The high peak power pulses of electrical energy are used to create intense pulses of light or high electric field, which have sterilising effects. By using the pulses to ionize a xenon gas lamp, broadband "white" light, of wavelength in the range from 200–1100 nm (far-UV to infrared) can be emitted.

In a most preferred embodiment, the sterilising means comprises at least one ultraviolet light emitting source mounted in the chamber, and the sterilising means is arranged on the closure of the enclosure. To ensure an even distribution of the UV light in the sealed chamber, more than one UV light source may be used. Where three or more sources are used, these may be arranged parallel to one another and spaced apart from one another by equal or unequal distances.

In the arrangement of the invention, a container holding sterile material can be coupled to a sterile process enclosure and the sterile material can be transferred to the process enclosure without compromising the sterility of either the material or the process enclosure. This is achieved by connecting the closed container, the external surfaces of which are not sterile, to a port on the exterior of the process enclosure so that a sealed chamber is created between them. This sealed chamber is not sterile, but can be sterilised prior to the opening of respective doors or closures in the container and the process enclosure, preferably by irradiating the sealed chamber with ultraviolet light generated from a source which is mounted on the door of the enclosure. Once the sealed chamber has been sterilised, any doors and closures opening to the chamber may be opened or removed to provide a continuous sterile or containment passage between the interiors of the container and the process enclosure, enabling the sterile contents of the container to be transferred to the process enclosure.

A sensor device may be provided to detect when a connection between a container and the enclosure has been made to form a chamber and to initiate a sequence of steps to seal and sterilise the resulting chamber. The container and enclosure, once coupled, are locked together to avoid any accidental displacement of the container which would result in the integrity of the enclosure being compromised. In a preferred arrangement, an expandable seal is provided between the container and the enclosure and is expanded on coupling to form the sealed chamber and to lock the container and enclosure together. Most preferably, the container includes a male element of circular cross-section and the expanded seal bears radially between the male element and a correspondingly shaped female element of the enclosure to lock and seal the container and enclosure together. A second expandable seal is preferably provided to retain the container and enclosure sealed together in the event of failure of the main seal. A supplementary mechanical locking device is preferably provided to locate the male part in the female part and to allow the seals to inflate in the correct location. The male element advantageously comprises a collar of stiff material and may, for example comprise moulded polypropylene or polyethylene.

The transportable container conveniently comprises a heat resistant container, at least a portion of which is fabricated from a porous material having pore sizes of less than about 0.2 micrometers. The container can thus be sterilised by heat sterilisation as the porous material permits the passage of steam but not of microorganisms.

The closure of the container may be positioned in such way that when the container is coupled to an enclosure, the contents of the container fall under gravity toward the closure. This arrangement facilitates the discharge of the contents from the container into the enclosure and is particularly advantageous when the contents are numerous and/or heavy. To facilitate further the gravity feed of the container contents to the enclosure, the port of the enclosure may be angled inwardly downwardly and the container closure may likewise be angled to act as a chute for the discharge of the contents.

A particularly convenient arrangement according to the invention includes a set of UV light sources disposed on the closure door of the enclosure, the arrangement being such that when the door is closed, the UV sources are so located to direct UV light away from the door toward the container. Deflective shielding is provided between the UV lamps and the door to reflect the UV light travelling toward the door back toward the exterior, to maximise the UV dosage in the sealed chamber in use. Most preferably, the deflective shielding is curved so that each UV lamp rests substantially in a trough of the shielding.

A diffuser is advantageously provided between the array of UV light sources and the exterior and this serves a number of purposes including (a) diffusing the UV light to give a more even distribution of light in the sealed chamber; (b) protecting the UV lamps from damage and (c) allowing easy cleaning. One suitable material for the diffuser is plate or sheet quartz, for example quartz sheet of thickness 3.175 mm (⅛ inch) thick. Other UV transparent materials will be suitable for this purpose.

The UV light dosages required to kill microorganism, including bacteria, fungi, yeasts, spores, viruses and algae are known in the art. With the arrangement according to the invention, using an array of four UV lamps emitting at a total of 12 watts at about 254 nm, we have typically recorded a minimum UV light intensity of 8,000 microwatts/$cm^2$/second on the side of the diffuser sheet distal the UV lamps. Spores of *Bacillus subtilis* are killed by a dosage of 22,000 microwatts/$cm^2$ and therefore, an irradiation time of about 3 seconds is adequate to kill *Bacillus subtilis* spores and to achieve a millionfold ($10^{-6}$) reduction in the occurrence of viable spores. The duration of the irradiation can be chosen to ensure that a dosage adequate to destroy contaminants of concern is delivered.

Thus, the apparatus and process according to the invention provide means for effecting the sterile docking of a transportable container with an enclosure at ambient temperature and pressure using an inexpensive container which need not be manufactured to highly toleranced engineering specifications. Using UV light or pulsed light to sterilise a passage formed between the container and the enclosure allows all exposed surfaces to be sterilised prior to opening the closures or doors to permit communication between the respective interiors. The arrangement of the docked elements is such that all relevant non-sterile surfaces are presented for sterilising with no shadowing occurring.

The invention will now be described more particularly with reference to the accompanying drawings in which:

FIG. 6 is a detailed view of the circled area of FIG. 4a;

Figure 1:
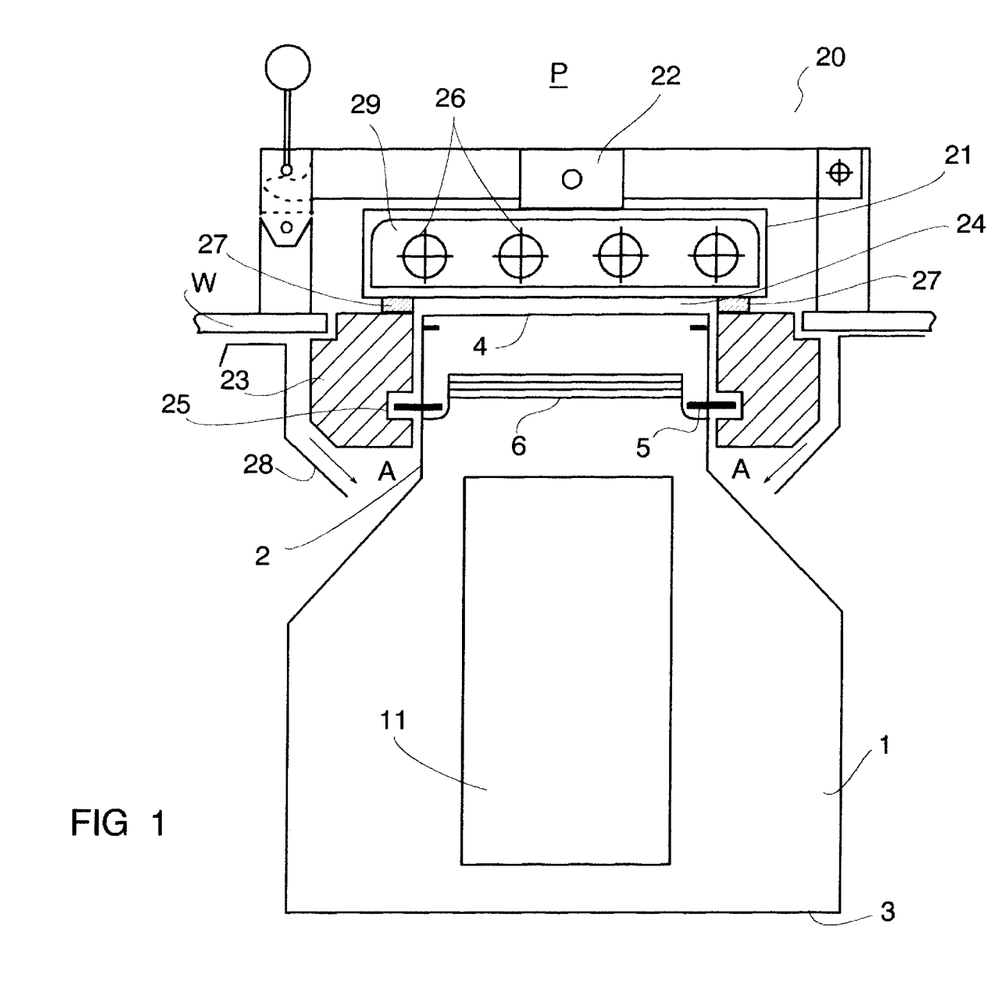
FIG. 1 is a partial sectional view showing a transportable container docked with a production enclosure.

FIG. 1 shows in partial section a component transfer container 1 docked with a port 20 located in a wall W of an enclosed production enclosure P. The container 1, which is composed of heat resistant plastics material is provided with a panel 11 of a porous material which is permeable to steam but impermeable to contaminants such as bacteria or other particulates. Suitable material for the panel is a heat resistant porous web having pore sizes of less than 0.2 micrometers. One such material is Tyvek (Trademark), manufactured by Du Pont. Provided that the porous material is of sufficient strength, the whole container may be fabricated from the porous material. The interior of the container 1, together with its contents, may be sterilised by autoclaving, for example at about 121° C. for about 40 minutes. Thus components or material, once loaded into the container, can be sterilised by autoclaving and maintained sterile while within the container, even during transfer between the autoclave and the manufacturing site. Such transfers can then occur in pharmaceutically uncontrolled or unclassified spaces. Components are placed in the container 1 either via the mouth 2 or preferably via an optionally provided opening in the base 3. Where such an openable base 3 is provided, then this is heat sealable for autoclaving and transport.

The mouth 2 is comprised of a refractory material such as glass, heat resistant plastics material, steel or the like to which is bonded the porous material of the container 1 which is normally, but not exclusively, flexible. The mouth is sealed by at least one closure 4 normally but not exclusively comprising the same porous material as that of the panel 11. Optionally, a lid or cap (not shown) may be provided to fit over the end of the mouth to protect the integrity of closure 4 by minimizing the potential of recontamination with bioburden after autoclaving (or other sterilising) and during transport.

In a preferred embodiment, the container 1 is supplied pre-assembled with its closure or closures 4 and preferably with a lid and has an opening in the base 3 for filling the container. In this preferred embodiment, there is consequently no need to tamper with the mouth of the container, which docks in use with a port 20 of a sterile production area P in the manner which is described below.

Components or material may be loaded into the container 1 and sterilised in a remote location, then conveyed to a user in another site for downstream processing. Alternatively, components may be placed in the container and sterilised on site for transfer to a downstream process on the same site. It is particularly advantageous that the container can be subjected to sterilisation by autoclaving as this is a preferred method of achieving sterility of components in many pharmaceutical applications. Sterilisation of the container interior is also achievable by other known means, such as gamma or E-beam irradiation and in cases where irradiation is used for sterilisation, then there is no necessity to provide a panel of porous material in the container. For on-site sterilisation, autoclaving is preferred for its reliability and ability to achieve the high sterility assurance levels desired by this industry. It is also the case that in many instances, a change from sterilisation by autoclaving to other methods would require very costly verification procedures to ensure that the new method meets the safety requirement of the original product authorisation. In consequence, holders of product authorisations are extremely reluctant to deviate from the already approved methodologies.

Transfer of the components between the container 1 and the sterile production enclosure P may be understood by reference to FIG. 1. In the following description, a sterile transfer of sterile components from the container 1 to the sterile production enclosure P will be described, but it will be evident that equally the transfer may be from the sterile production enclosure P to the container 1. The port 20 located in the wall W of the sterile production enclosure P includes a door 21 which includes an array of UV sources 26 and which opens about the over centre hinge 22 to provide access to the space P. On the side of the door 21 distal the space P, the port 20 is provided with a docking assembly 23, which together with the door 21, defines about and below the UV sources 26 a UV chamber 24. The docking assembly 23 includes a pair of recesses 25 for receiving a pair of lugs 5 provided on the exterior surface of the mouth 2 of the container 1. The recesses 25 are accessed via slots (not shown) in the docking assembly, the slots being arranged perpendicular to the recesses 25 so that when the lugs 5 are offered up to and travel to the ends of the slots, a rotational movement of the mouth 2 brings the lugs 5 into engagement with the recesses 25, so as to lock the container 1 securely and sealingly to the port 20. Once locking is effected, the array of ultra violet sources or lamps 26 mounted within the UV chamber 24 by attachment to the door 21 is activated to sterilise the interior of the docking assembly 23, including those surfaces of the container 1 facing the UV sources 26. Provision of a reflector 29 behind the UV sources 26 ensures that the UV light is reflected into the chamber 24. After a predetermined time, the lamps are switched off, the door 21 is opened and the closure 4 is removed manually by an operator acting from within the sterile production enclosure P. Alternatively, with the UV lamps still on and the door 21 still closed, any lids and closures 4 over the mouth 2 of the container are removed one by one, with a period of irradiation allowed between each removal to ensure sterilisation of newly exposed surfaces. In either case, when each closure 4 has been removed so that the mouth 2 of the container 1 is now open, the door 21 is opened to provide free access between the interiors of the container 1 and the production enclosure P. The contents of the container 1 can then be displaced into the production area P via the mouth 2 and optionally a chute 6 formed with the mouth 2. Once the container is emptied, the door 21 is closed and the container 1 can be removed from the port 20 and discarded or recycled as appropriate. If desired, the container 1 may be left docked with the port 20 for receipt of materials from the production enclosure P for transfer to another downstream process area.

A ring seal 27 is provided in the docking assembly 23 at the position in an opening of wall W to prevent contamination occurring at this point. To prevent this seal constituting a possible source of contamination, the UV lamps 26 are arranged so as to irradiate the externally facing surfaces of the seal 27. It is also envisaged that a cover (not shown) be provided to engage the container-receiving opening of the docking assembly 23 so as to restrict contamination of the UV chamber 24 when not docked with a container 1.

The docking assembly 23 includes deflecting baffles 28 which engage about the container 1. Air is blown about the baffles 28 in the direction of the arrows A to blow from the UV chamber any particulate material which might otherwise contaminate the interior of the container or sterile process enclosure after docking. Alternatively, the same effect may be achieved by drawing a vacuum in the UV chamber 24 after docking.

Figure 2:
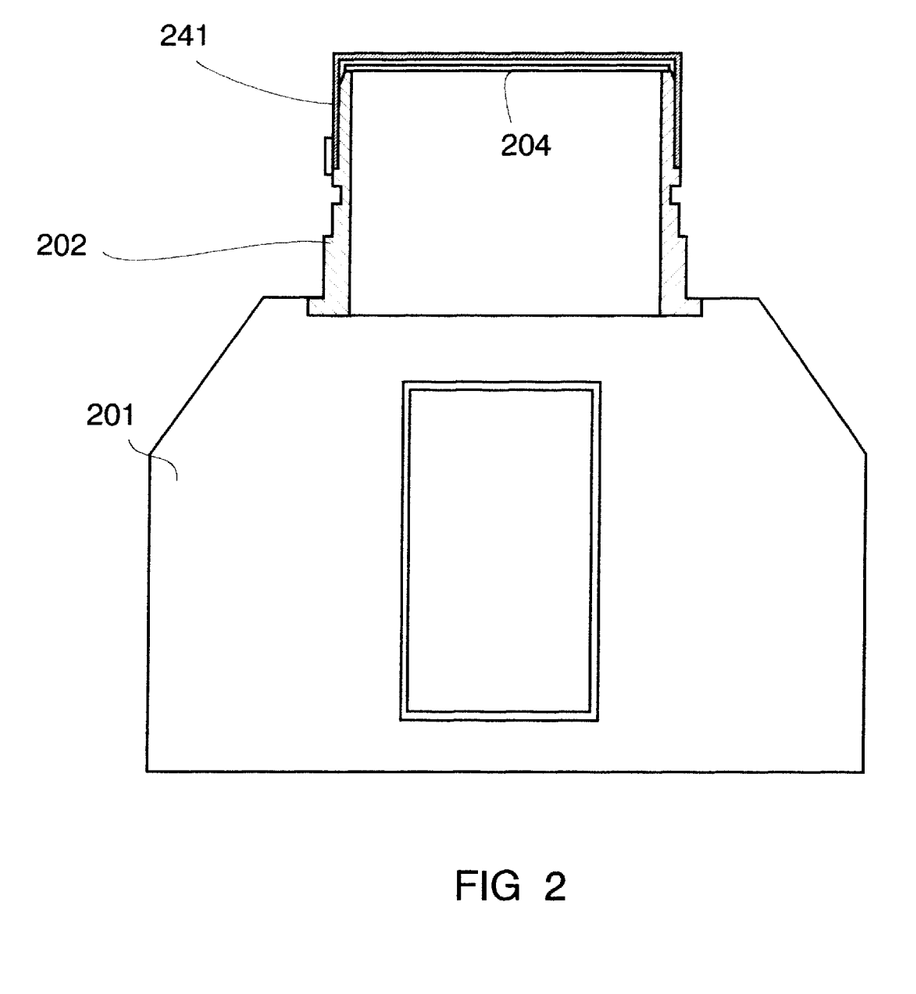
FIG. 2 is a sectional view showing an alternative embodiment of a container.
Figure 3:
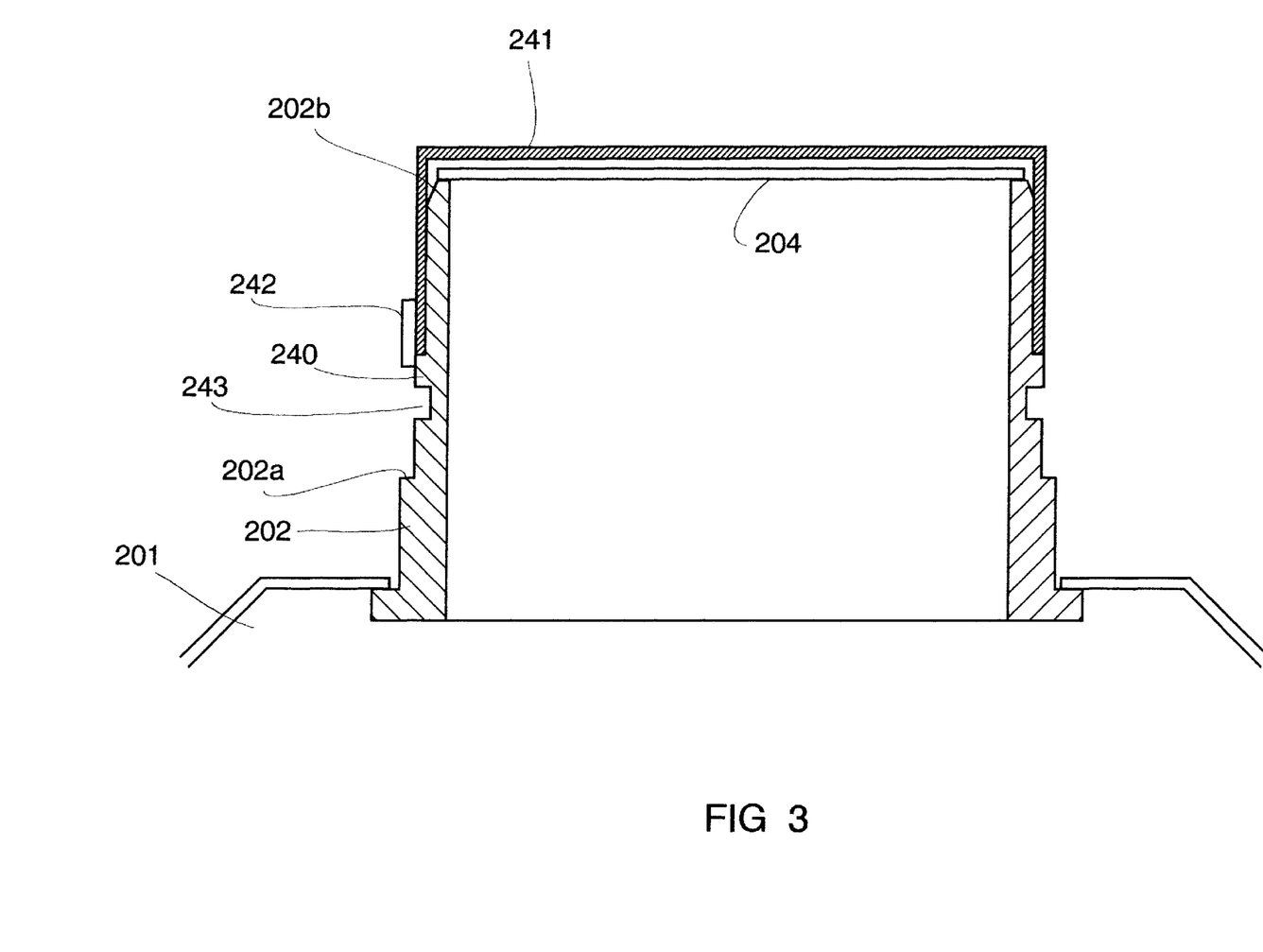
FIG. 3 is a detailed view of the mouth area of the container of FIG. 2.

Referring now to FIGS. 2 and 3, a transportable container 201 includes a mouth 202 of circular cross-sectional shape. A peelable foil closure 204 is sealed over the mouth 202 and during transport, a cover 241 is placed over the mouth 202 and foil closure 204. The bag (and contents) are sterilised by suitable means, ensuring that the area of the mouth 202 under the cover 241 (FIG. 3), including the underside of a grippable tab (not shown) of the foil closure 204, is sterile.

As shown more clearly in FIG. 3, the wall of the mouth 202 is provided with a resilient radially extending stop 240 over which the cover 241 fits as a snap-fit. A tape 242 is wound about the junction between the stop 240 and the cover 241 to afford additional protection against the ingress of contaminants. Shortly before the container 201 is to be docked with an enclosure, the tape 242 is peeled off and the cover 241 removed.

Figure 4A:
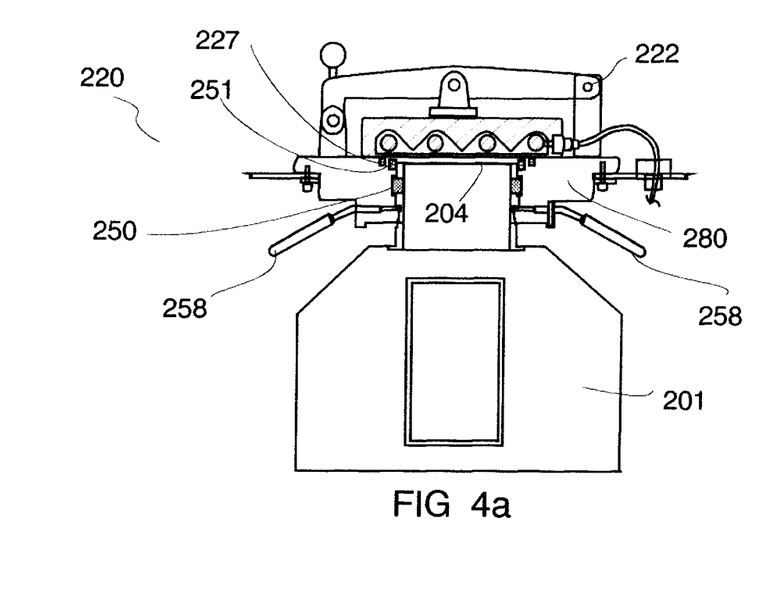
FIG. 4a is a sectional view of the container of FIGS. 2 and 3 docked with a production enclosure and FIG. 4b is a plan view thereof.
Figure 4B:
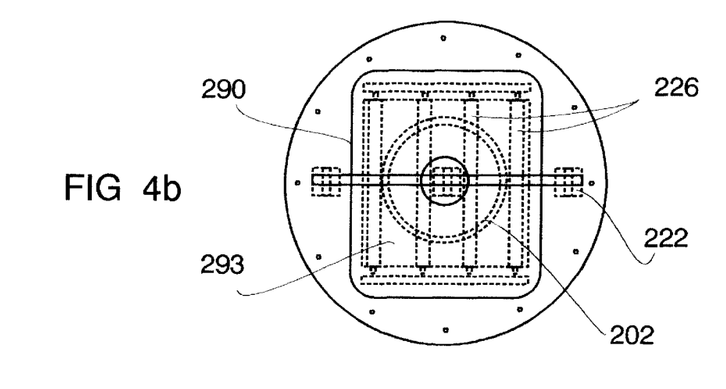
Figure 5:
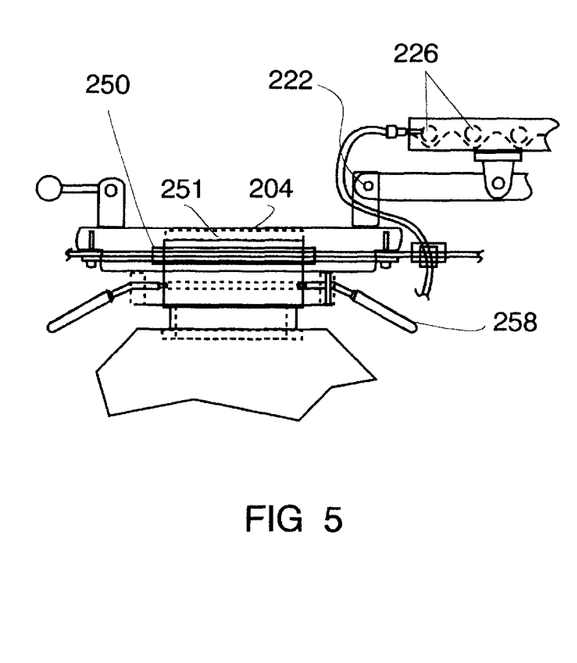
FIG. 5 is a view similar to FIG. 4a, with the door shown open.
Figure 6:
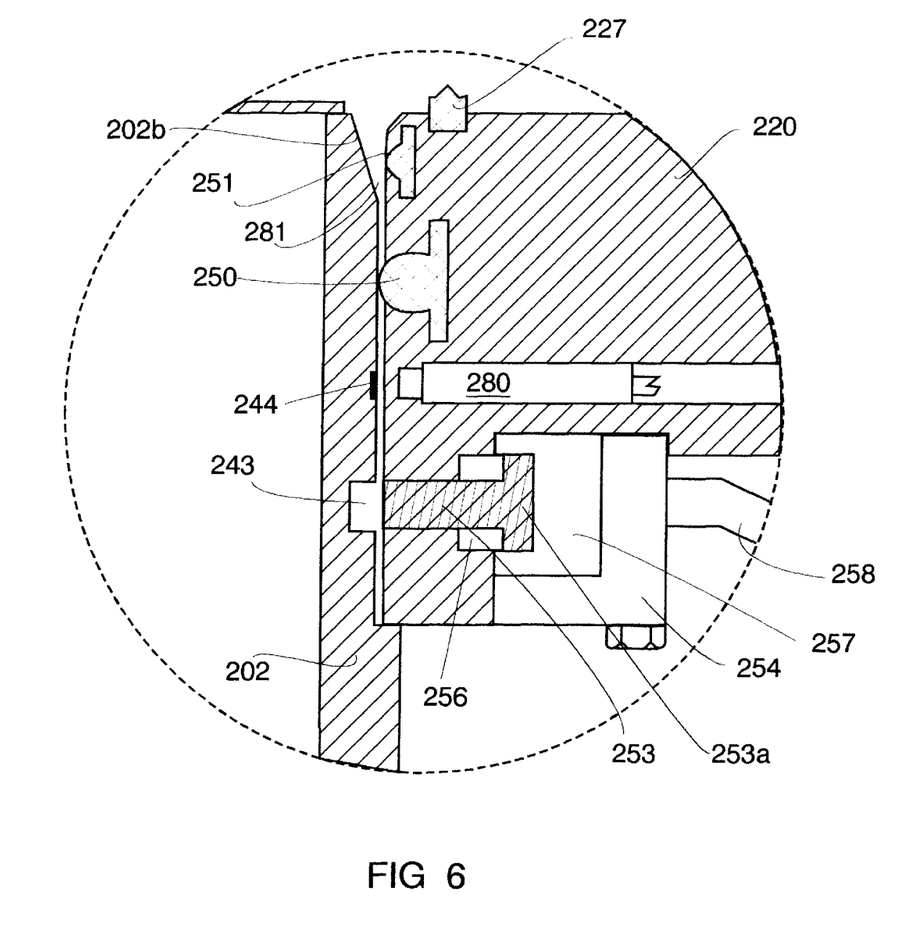

Referring to FIGS. 4 to 6, the port 220 of a production enclosure includes an expandable locking seal 250 and an expandable neck seal 251 in addition to a ring seal 227. A locking mechanism for the parts includes a set of four radially equidistantly spaced apart pins 253 held in a housing 254 of the port 220. A through-bore 255 in the port 220 enables the pins 253 to be moved into locking engagement with a radial groove 243 of the mouth 202 (see FIG. 3). The head 253*a* of each pin is biased by spring 256 into engagement with a cam surface 257, connected to handle 258. To lock the mouth 202 with the port 220, the handles 258 are rotated about their longitudinal axes, causing the pin heads 253*a* to move relative to the cam surfaces 257 to displace the pins 253 into the groove 243. A releasable lock (not shown) locks the pins 253 in position, securing the mouth 202 and port 220 together.

Figure 7:
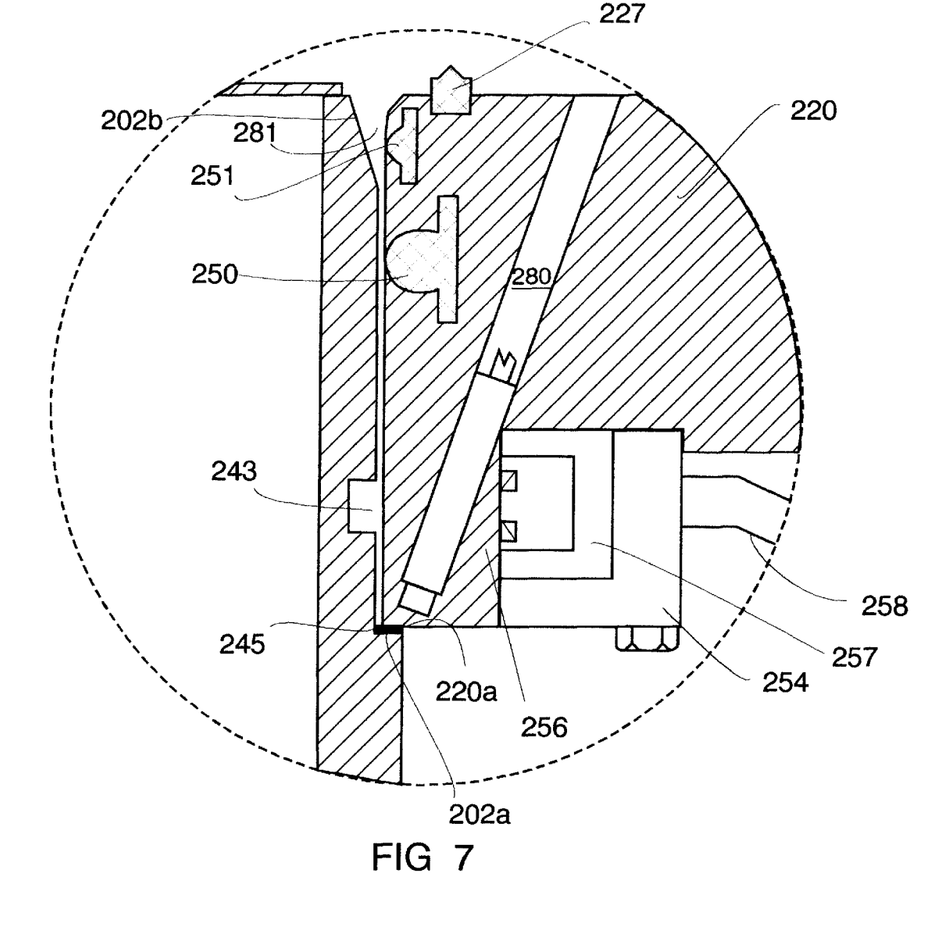
FIG. 7 is a view similar to FIG. 6, showing an alternative arrangement of the sensor.
Figure 8A:
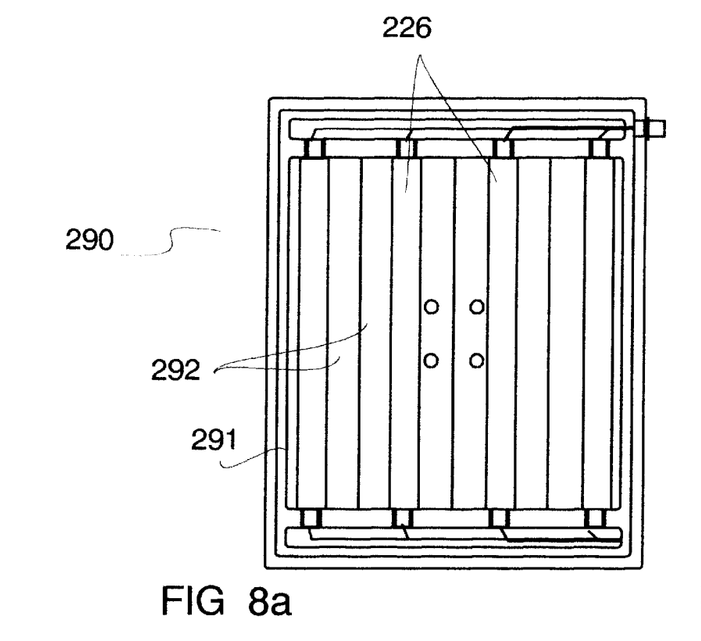
FIGS. 8a and 8b are respectively plan and sectional views of the UV lamps array of FIGS. 4 and 5.
Figure 8B:
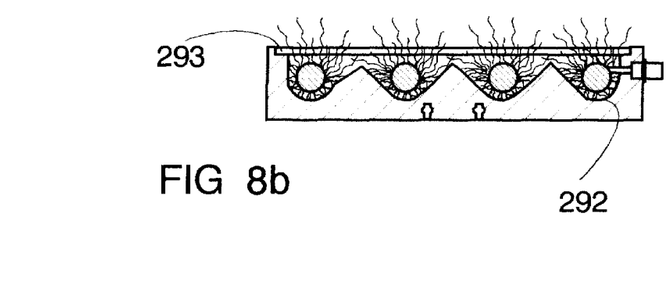
Figure 9A:
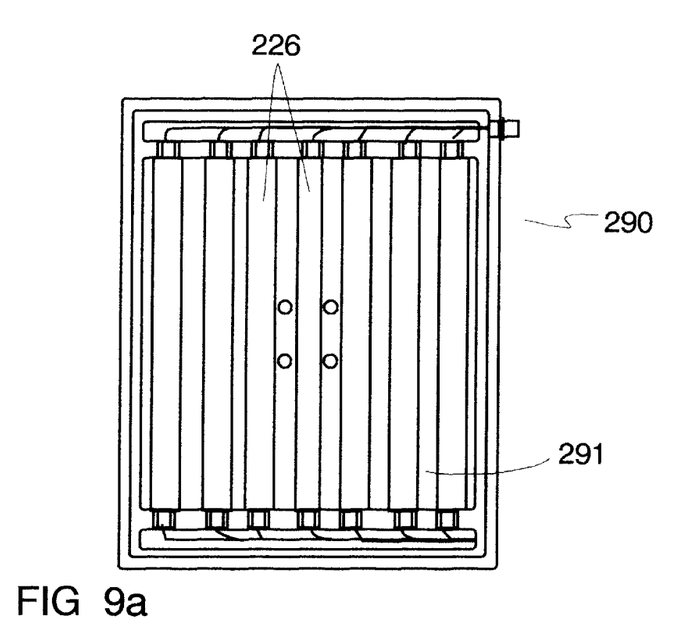
FIG. 9a and 9b are views similar to FIGS. 8a and 8b of an alternative arrangement of the UV lamp array.
Figure 9B:
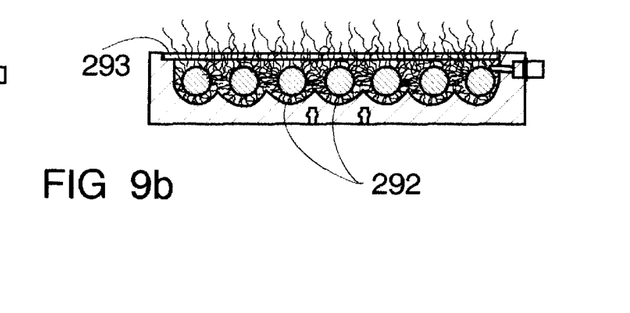

The mouth 202 includes a shoulder 202*a* which acts as a stop to prevent the mouth 202 being pushed too far into the port 220, by abutting a lower edge 220*a* of the port 220. A sensor 280 is provided in the port 220 to detect when the mouth 202 is located in the port 220. As shown in FIG. 6, the sensor may detect a circumferentially extending conductive strip 244 arranged on the mouth 202 and initiate the locking and/or irradiation cycle. Alternatively, as shown in FIG. 7, a conductive strip 245 may be placed on the shoulder 202*a*.

Once the port 220 and mouth 202 are locked together by the engagement of pins 253 in groove 243, the expandable locking seal 250 is inflated to bear radially against the mouth 202. This seal serves both to seal and lock the parts together. A cycle of irradiation is used to sterilise the area 281, then expandable neck seal 251 is inflated and a further irradiation cycle is conducted. The upper wall 202*b* of the mouth 202 is tapered inwardly to facilitate irradiation and avoid shadowing. The ring seal 227 provides a seal between the port 220 and the quartz diffuser plate 293 of the UV array of the door. As in the embodiment of FIG. 1, the seal 227 is seated in the wall of the port 220 and all of its exposed surfaces are sterilised during the irradiation cycle.

The event sequence for docking the container 201 and port 220 will now be described, with particular reference to FIGS. 10 to 14.

Figure 10:
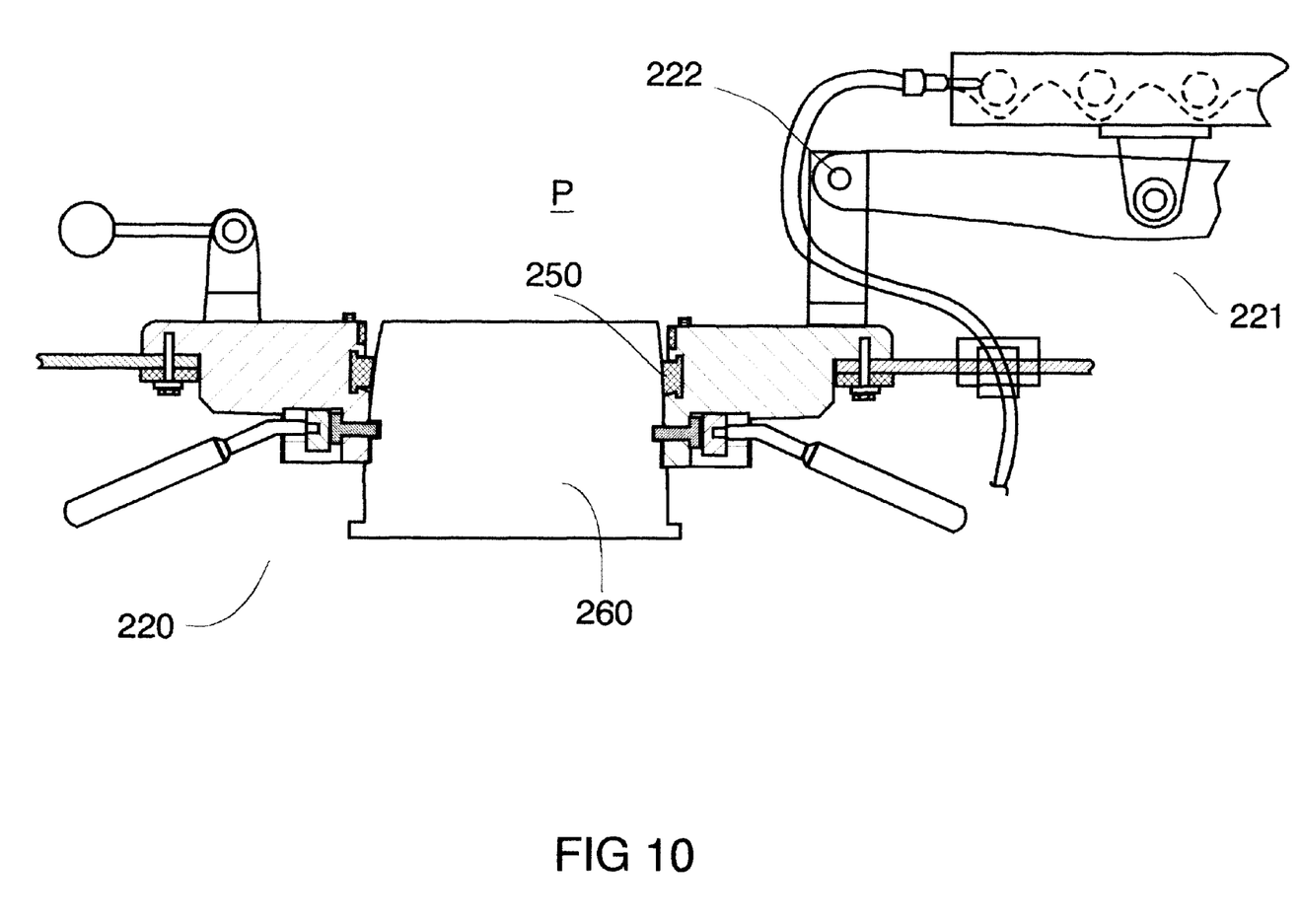
FIGS. 10 to 14 show the sequence for operating the coupling.
Figure 11:
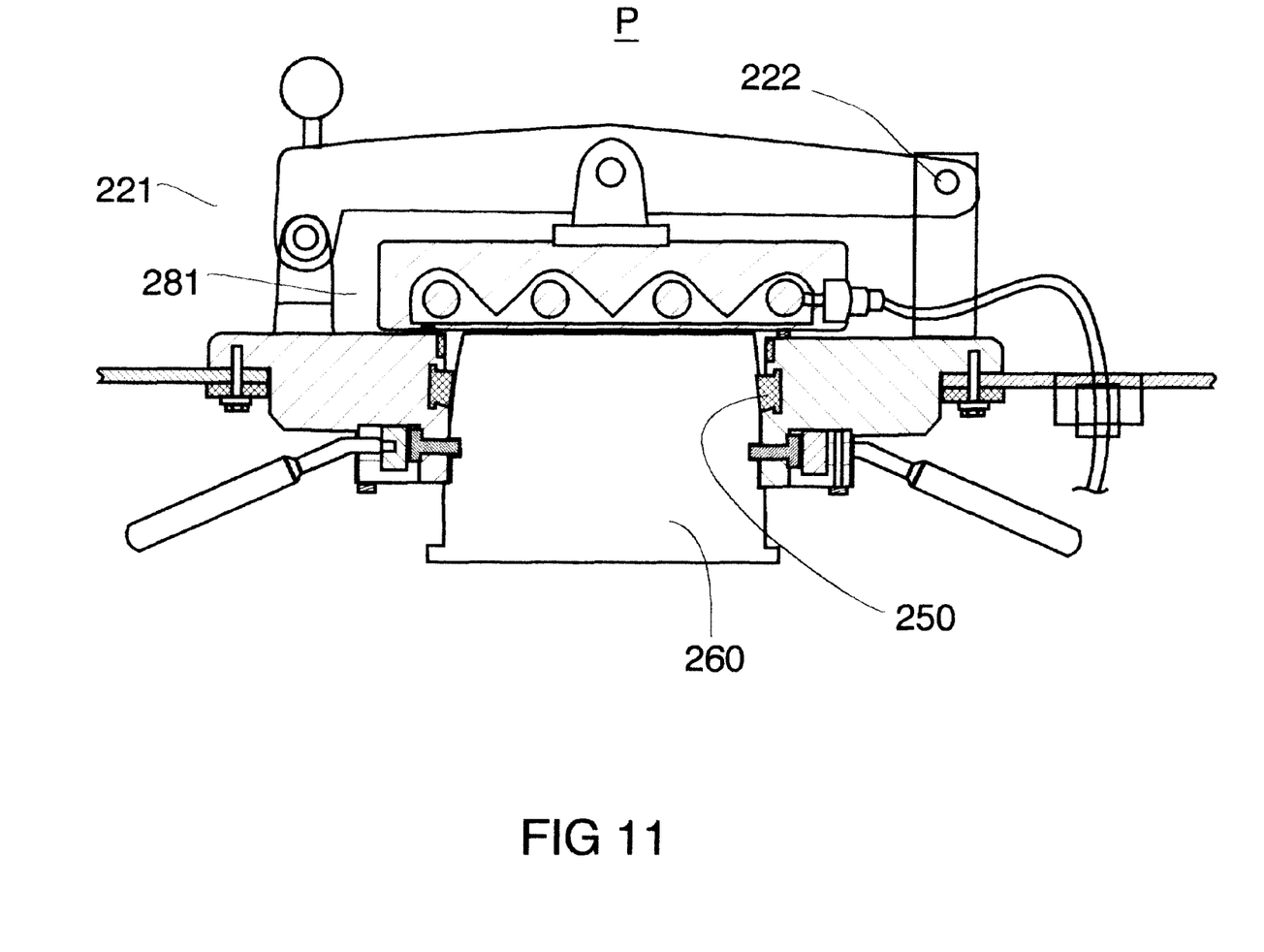

As shown in FIG. 10, for example in a start-up condition, a closed bung 260 which otherwise has the features of the mouth 202 which enable it to engage the port 220, is located in the port 220 and at least the locking seal 250 is inflated. The door 221 is open so that the UV lamp array faces into the interior P of the production enclosure. The interior is then treated and the door (now sterile) is closed, as shown in FIG. 11, which shows the normal configuration of the port 220 between transfers. The bung 260 is retained in place to protect the now-outwardly facing UV array from accidental damage.

Figure 12:
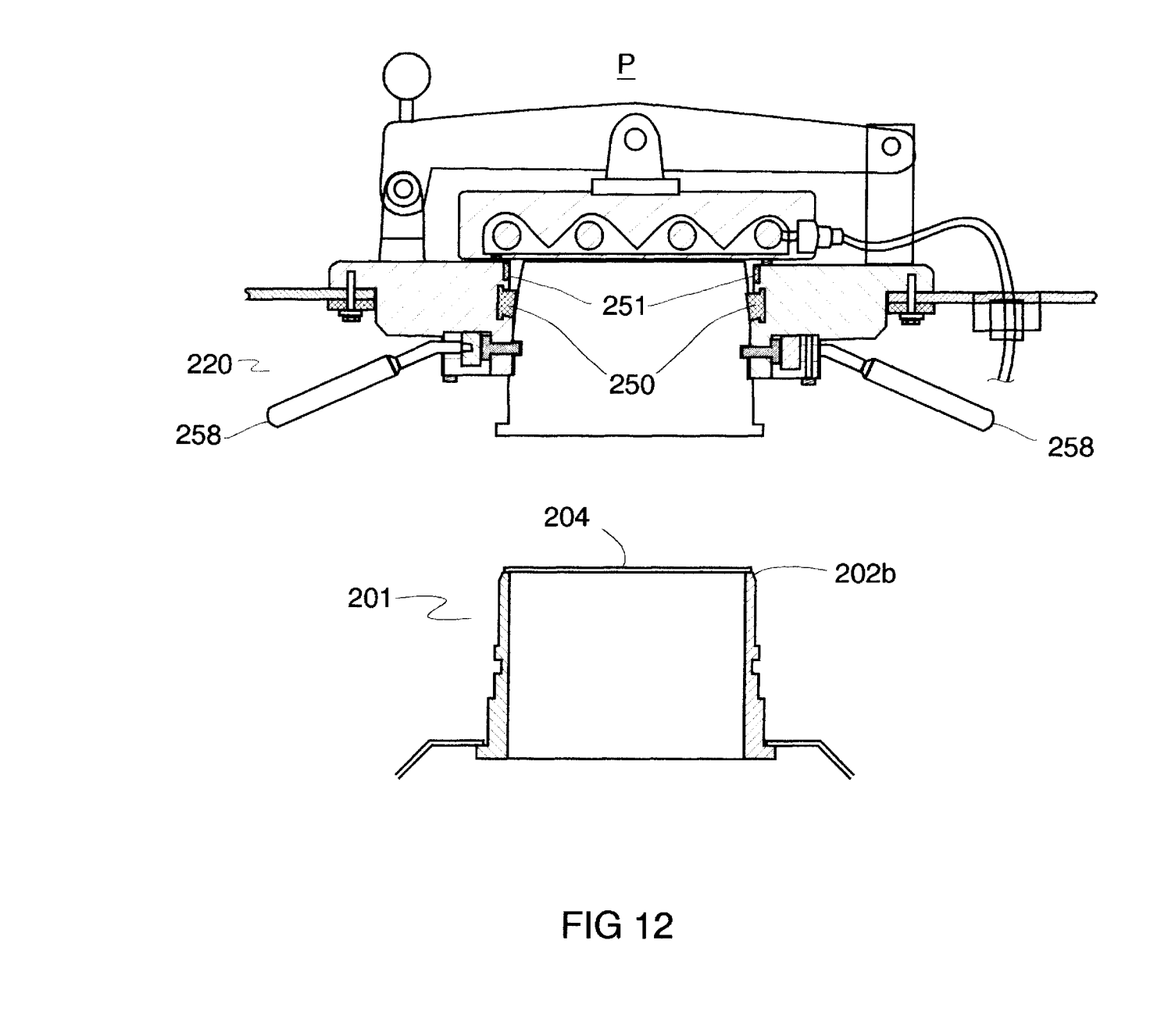
Figure 13:
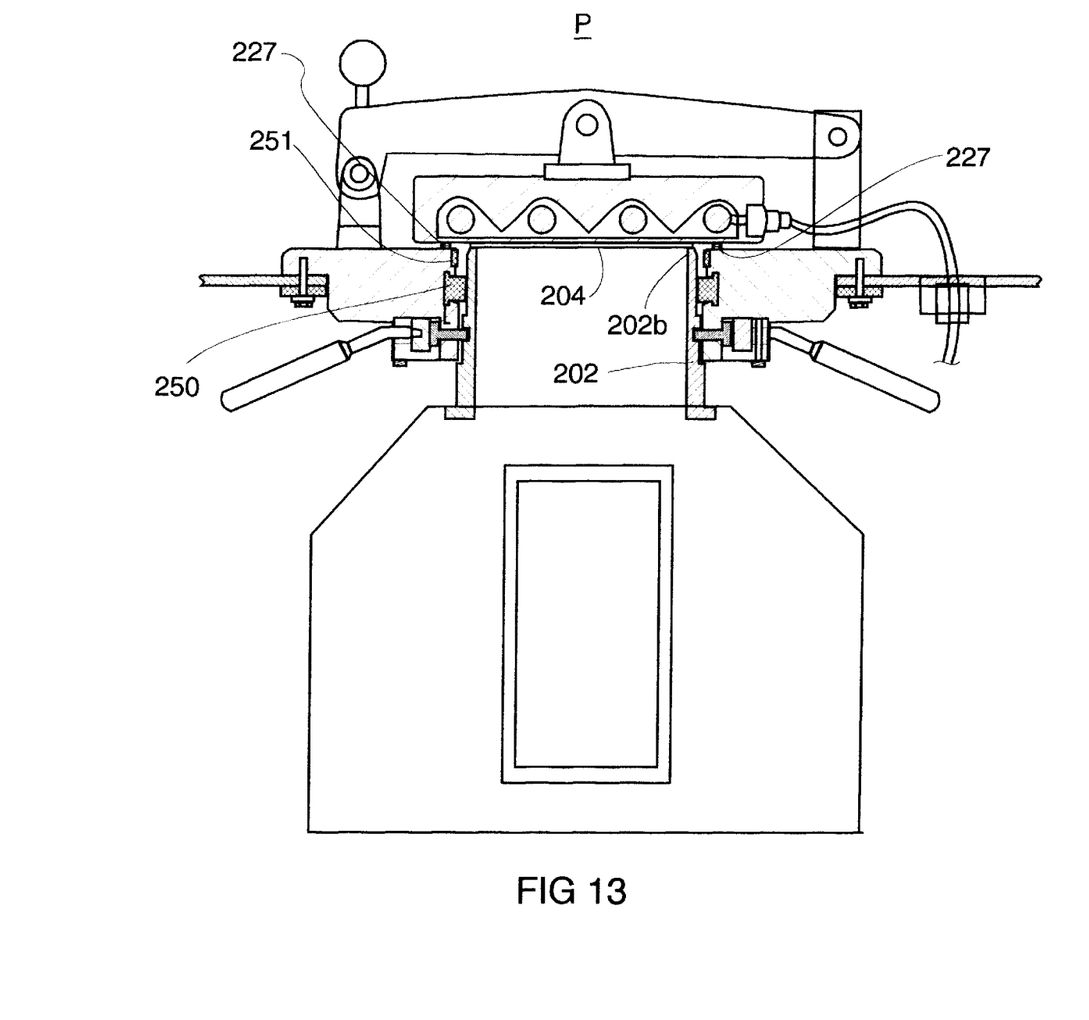
Figure 14:
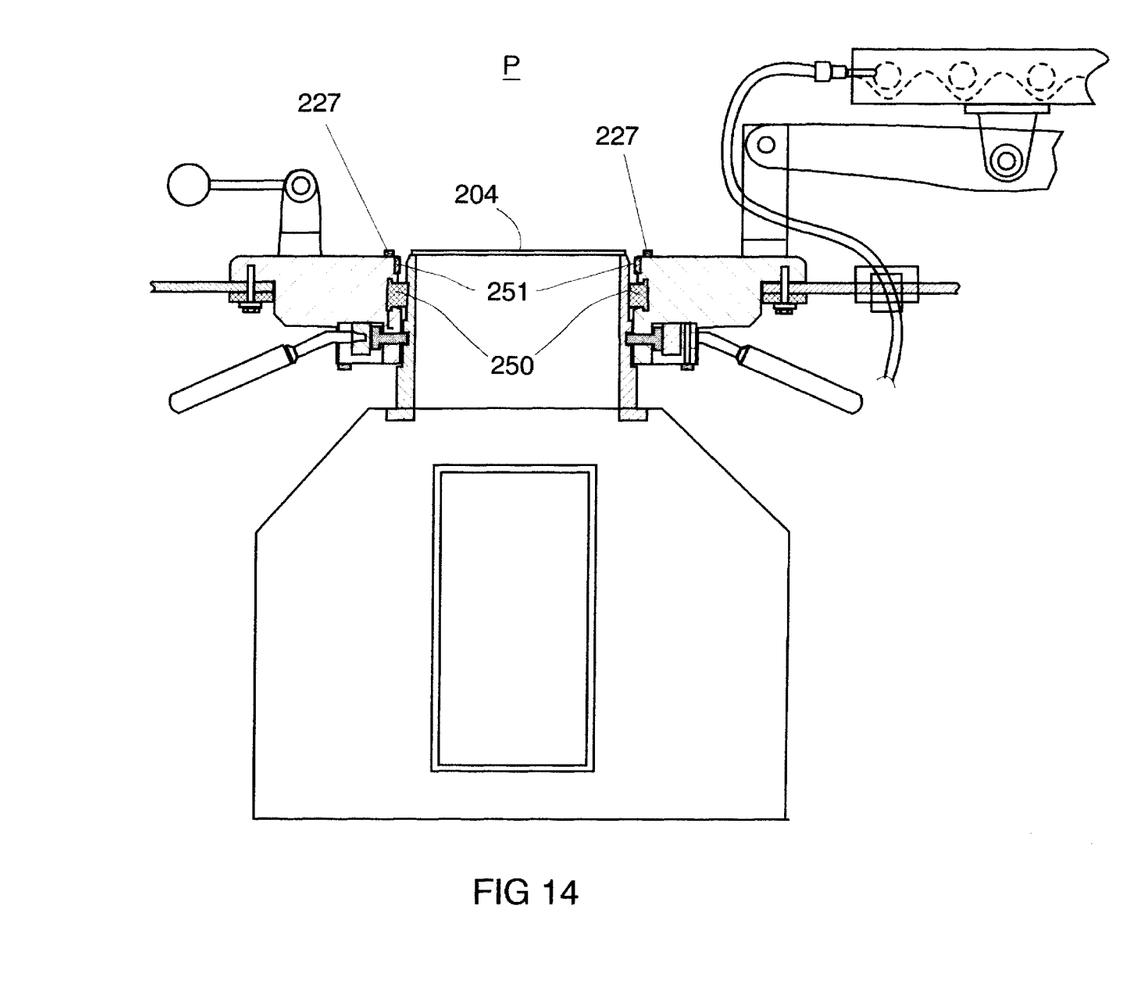

When a transfer is to be made, the bung 260 is removed from the port 220 and the tape 242 and cover 241 are removed from the mouth 202 of the internally sterile container 201. As shown in FIG. 12, mouth 201 is offered up to the port 220, the handles 258 are rotated to lock the parts together and the UV irradiation sequence is begun, either manually or automatically as described above. In the latter case, the sensor 280 detects when the mouth 202 is correctly located in the port 220 and automatically initiates the remainder of the sequence. Once location is effected, the expandable locking seal 250 is inflated (FIG. 13) to seal the space 281 between the exterior of the mouth 202 and the interior of the port 220.

The sealed space 281 and exposed surfaces between the opening of mouth 202 and locking seal 250 are then sterilised by activating the array of UV lamps 226 for a desired length of time. As described above, the mouth 202 is tapered at 202b toward its opening to facilitate effective irradiation of its external walls and to avoid UV shadowing. Next, the expandable mouth seal 251 is inflated and another cycle of UV irradiation is conducted. The area between the port 220 and the mouth 202 is now sterilised and the door 221 is opened inwardly (FIG. 14) into the enclosure about the hinge 222. Finally, the foil closure 204 is removed.

While they are inflated, the seals 250 and 251 each provide a barrier between the interiors and exteriors of the mouth 202 and port 220 and additionally, each contributes to the locking of these parts together. Indeed, this locking effect in itself is sufficient to retain the parts together without any other locking mechanism. Nevertheless, for increased security of the interconnection, it is preferred to have a supplementary locking mechanism, such as that afforded by the engagement of the pins 253 in the groove 243.

Although the seals 250 and 251 have been described as expandable seals, it will be appreciated that other means for achieving the desired sealing/locking effect are possible. For example, seals which can be spring biased into a sealing/locking position may be used.

The UV lamp array will now be described in more detail with reference to FIGS. 4, 5, 8 and 9. The embodiment shown in FIGS. 4, 5 and 8 includes 4 UV lamps, while that of FIG. 9 has 7 lamps. In each case, the UV lamps 226 are mounted in a housing 290 which includes a sinusoidal-shaped deflector 291. Each lamp is located in a trough 292 of the deflector 291 and the walls of the trough serve to reflect UV light toward the diffuser 293, as shown by the lines in FIGS. 8b and 9b. The diffuser 293 comprises a transparent sheet of quartz of 3.175 mm thickness. The quartz sheet serves to diffuse the incident UV light emitted toward the mouth 202 of the container and to protect the UV light sources. Sheets of greater or lesser thickness of quartz may be used, as required.

EXAMPLE

The intensity of the ultra violet light on the face of a 3.175 mm quartz sheet was measured. Readings were made on the side of the sheet distal from the UV sources and at a distance of 2.8575 cm from the face of the sheet.

The UV array was configured as shown in FIGS. 2 to 6 and 8 and included 4 UV lamps emitting at 254 nm, obtained from Light Sources, Inc., Milford, Conn., USA. Measurements were made using a UV RADIOMETER detector Ser. No. 9811 obtained from Cole-Parmer Instruments, Chicago, Ill., USA. The test surface comprised a flat grid and a 15.24 cm outer diameter circle. The quartz glass sheet was supplied by Technical Glass Products, Mentor, Ohio, USA.

Figure 15:
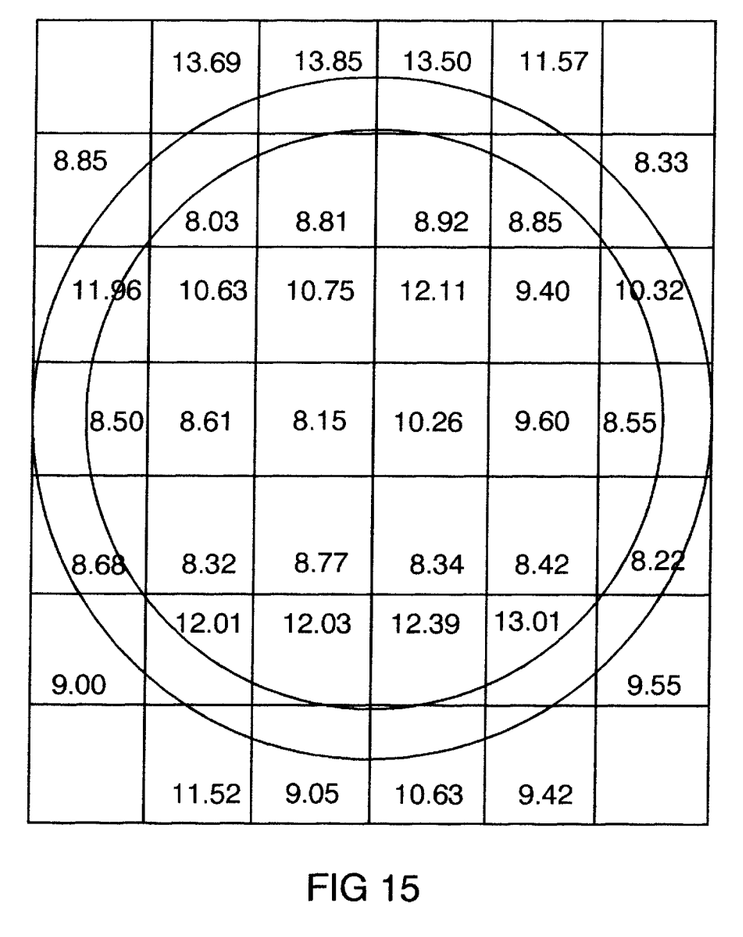
FIG. 15 is a table showing light intensities measured from the array of FIG. 8.

The results are shown in FIG. 15. The circle drawn on the figure represents the area of the mouth of the transportable container and includes the area of the seal 227 (see, for example, FIG. 13). Units marked are expressed in microwatts/cm$^2$/second. It will be seen that the dosages of UV radiation delivered across the quartz sheet are high and appropriate duration of the exposure can be selected to kill specific target microorganisms. The inner diameter of the mouth part of the container in this case was 12.7 cm. Thus, it can be seen that good UV dosages are delivered to the area to be sterilised, including the exposed faces of the seal 227.

UV or pulsed light irradiation is preferred as an effective, inexpensive and relatively safe sterilisation means.

Some advantages of the transfer system described are as follows:

(1) The transfer container is inexpensive to produce and may be manufactured from biodegradable material. In suitable applications, the container may be recycled.

(2) Transfer using the system can be effected with a high level of sterility assurance, $10^{-6}$ being achievable.

(3) The container can be autoclaved, or may be sterilised by other known means such as gamma or electron-beam irradiation, steam, ethylene oxide gas or vapour phase hydrogen peroxide.

(4) Since the container can dock directly with an isolated and/or contained process enclosure, the need for an intermediate laminar flow cabinet between the sterilisation area and the process enclosure is avoided.

(5) Since the size of the mouth of the transportable container is not limited by manufacturing tolerances, the connection between the sterile process enclosure and the transfer container can be of any desired size. Equally, the connection can be of any desired shape.

It will of course be understood that the invention is not limited to the specific details described herein, which are given by way of example only, and that various modifications and alterations are possible within the scope of the invention as defined in the appended claims.

I claim:

1. A coupling assembly for use in sterile transfer of sterile materials between a transportable container and a sterile enclosure, the assembly comprising sterilizing means, a first coupling member on the container engageable with a second coupling member on the enclosure and engaging means associated with each of the coupling members for sealingly interengaging the container and the enclosure, the first coupling member including a removable container closure and the second coupling member including a removable closure for the enclosure so that on interengagement the closures define between them a sealed connecting chamber, the sterilizing means comprising means for generating sterilizing ultraviolet or pulsed light radiation and being contained substantially within the sealed connecting chamber and being operable to generate in the chamber ultraviolet light or pulsed light radiation for sterilizing the chamber and its internal surfaces.

2. The assembly according to claim 1, in which the second coupling member includes the sterilizing means, the sterilizing means being mounted so as to face toward the first coupling member.

3. The assembly according to claim 2, in which the second coupling member includes a docking element for releasably engaging the first coupling member, the docking element surrounding the closure and the closure comprising a door which is openable inwardly into the enclosure to permit communication between the interiors of a docked container and enclosure on displacement of the closures, the sterilizing means being mounted on the door.

4. The assembly according to claim 3, in which a barrier means is provided between the door and the docking element and about the door to form a seal between the door and the docking element, and the sterilizing means is arranged to sterilize any exposed surfaces of the barrier means.

5. The assembly according to claim 4, in which the sterilizing means comprises at least one source of ultraviolet light and comprises at least 3 ultraviolet light sources arranged in parallel.

6. The assembly according to claim 5, in which the sterilizing means includes a deflector element for deflecting ultraviolet light toward the first coupling member, and in which the deflector element is formed with at least one elongate trough and each ultraviolet light source is mounted so as to lie substantially within the trough.

7. The assembly according to claim 6, in which the sterilizing means includes a diffuser element and the light source is located between the deflector element and the diffuser element.

8. The assembly according to claim 3, in which the docking element includes at least one sealing means for sealingly interengaging the first and second coupling members, the sealing means comprising an expandable seal which, on expansion, bears tightly between the docking element and the first coupling member so as to lock the enclosure and the container together.

9. The assembly according to claim 8, in which the docking element comprises a female element of substantially circular cross-section for receiving a correspondingly shaped male element of the first coupling member and in which the sealing means bears radially on the male element to seal and lock the first coupling member and the docking element together.

10. The assembly according to claim 3, in which the docking element includes supplementary locking means for locating the first coupling member in the docking element and for co-operating with locking formations of the first coupling member to lock the first coupling member and the docking element together.

11. The assembly according to claim 10, in which the locking formation comprises a circumferentially extending groove.

12. The assembly according to claim 1, including sensor means for detecting when the first and second coupling members are engaged, in which the sensor means includes means for effecting locking together of the first and second coupling members and in which the sensor means includes actuating means for operating the sterilizing means.

13. The assembly according to claim 1, including means for removing particulate material from the vicinity of the sterilizing means before or after engaging the first and second coupling members.

14. The assembly according to claim 1, including a protector for engaging the second coupling member in the absence of a first coupling member.

15. The assembly according to claim 1, in which the first coupling member includes a removable cover which fits about the closure to protect the closure from damage during transport or storage.

16. The assembly according to claim 1, in which the first coupling member comprises a collar of substantially rigid plastics material, and includes walls which taper inwardly toward a sealable mouth of the closure so that the external surfaces of the closure and of the walls are presented in the path of the sterilizing radiation without shadowing.

17. The assembly according to claim 1, including a transportable container and an enclosure, the container and the sterile enclosure being so formed or arranged that contents of the container can be fed between the interiors of the container and the sterile enclosure under the influence of gravity.

18. The assembly according to claim 1, including a container provided with a sealable opening for charging the container with contents, the opening being separate from the removable closure.

19. The assembly according to claim 1 in which the first coupling member includes a flange to which the body of the transportable container is sealed.

20. A process for conducting a sterile transfer of sterile materials between a transportable container and a sterile enclosure, comprising sealingly interengaging respective closures of each of the container and the enclosure to define between the closures a sealed connecting chamber, sterilizing the sealed chamber and its internal surfaces by generating in the chamber sterilizing ultraviolet or pulsed light radiation produced by sterilizing means contained substantially within the chamber and thereafter removing the closures of the container and enclosure to provide a path communicating between the interiors of the transportable container and the enclosure.

* * * * *